United States Patent [19]
Morris, Sr. et al.

[11] Patent Number: 6,148,229
[45] Date of Patent: Nov. 14, 2000

[54] SYSTEM AND METHOD FOR COMPENSATING FOR MOTION ARTIFACTS IN A STRONG MAGNETIC FIELD

[75] Inventors: G. Ronald Morris, Sr., Bay Shore, N.Y.; James W. Valentine, Spokane, Wash.

[73] Assignee: Medrad, Inc., Indianola, Pa.

[21] Appl. No.: 09/206,316

[22] Filed: Dec. 7, 1998

[51] Int. Cl.[7] .......................... A61B 5/0402; A61B 5/055
[52] U.S. Cl. ............................. 600/509; 600/411
[58] Field of Search ..................... 600/509, 411, 600/410; 128/901

[56] References Cited

U.S. PATENT DOCUMENTS

| | | | |
|---|---|---|---|
| 5,436,564 | 7/1995 | Kreger et al. | 600/411 |
| 6,043,650 | 3/2000 | Taniguchi et al. | 324/306 |
| 6,052,614 | 4/2000 | Morris, Sr. et al. | 600/509 |
| 6,073,041 | 6/2000 | Hu et al. | 600/410 |

OTHER PUBLICATIONS

"Optimizing Electrocardiograph Electrode Placement for Cardiac–Gated Magnetic Resonance Imaging" by Dimick et al., *Investigative Radiology*, Jan. 1987, vol. 2, pp. 17–22.

"ECG Monitoring in MRI to Detect Cardiac Ischemia", Request For Proposal By the Department of Health and Human Services, *Research Grant* (date unknown).

*Primary Examiner*—Kennedy Schaetzle
*Attorney, Agent, or Firm*—Amster, Rothstein & Ebenstein

[57] ABSTRACT

A system for monitoring an ECG during a patient examination in a strong magnetic field, such as that created by an MRI machine, which eliminates motion artifacts affecting the accurate reading of the ECG. The system modulates the strong magnetic field and then generates an error correction signal substantially equal to the motion artifact signal in timed relationship with the modulated signal that is subtracted from the measured ECG signal to produce a more accurate ECG signal.

9 Claims, 3 Drawing Sheets

SYSTEM AND METHOD FOR COMPENSATING FOR MOTION ARTIFACTS IN A STRONG MAGNETIC FIELD

FIELD OF THE INVENTION

This invention relates to instruments for making an electrocardiogram ("ECG") measurement of a patient in a strong magnetic field environment such as is found in MRI machines.

BACKGROUND OF THE INVENTION

Motion related artifacts, which interfere with the ECG signal presented to the ECG monitor, are common when using standard diagnostic type ECG equipment in a strong magnetic field environment, such as that presented in the tunnel of an MRI machine. FIG. 3A shows a representative normal ECG signal, while FIG. 3B shows a representative ECG signal including an error signal "e" (i.e., the voltage artifact) represented by the difference between the dotted line and the solid line therein.

One type of motion artifact is created by induction in the connecting leads or directly from the patient through the ECG electrodes. One example of this type of motion artifact is caused by patient breathing. The electrode leads, which are attached to the electrodes on the patient's chest, move in the strong magnetic field. Voltages are induced in the leads as a result of lead motion and are combined with the cardiac voltage at the input to the monitor. Another example of this type of motion artifact is one caused by patient blood flow. Since the blood is an electrical conductor that is moving in a magnetic field, rapid blood flow in the aorta and other large heart vessels generates interfering signals. This artifact combines with the cardiac voltage within the patient and is picked up on the skin by the ECG electrodes.

One method of correcting for motion artifacts in a ECG measurement made in the magnetic field of an MRI machine is described in an article in the January, 1987 issue of Investigative Radiology, entitled "Optimizing Electrocardiograph electrode Placement for Cardiac-Gated Magnetic Resonance Imaging" by Dimick et al. In this method, the ECG electrodes are placed in predetermined positions on the patient to minimize the motion artifact. The authors concede that this method is not totally effective in suppressing the blood flow artifact. Also, the detection of certain heart abnormalities requires that the ECG electrodes be placed in particular positions which may be inconsistent with the positions necessary for eliminating the motion artifact.

A second method for correcting for motion artifacts is described by a Request for Proposal by the Department of Health and Human Services, Research Grant entitled "ECG Monitoring in MRI to Detect Cardiac Ischemia" (date unknown). The Request for Proposal indicates that the National Heart, Lung, and Blood Institute is seeking "a device that can detect myocardial ischemia from the ECG (in the MRI environment) despite the voltages induced by blood flow artifacts." The Request for Proposal suggests that by "monitoring the ECG signals from an array of electrodes placed on the chest both before and after the patient is placed in the magnet . . . [t]he difference between these two sets of signals is due to the voltages induced by the rapid blood flow through a magnetic field [and] [d]igital signal processing might then be used to reconstruct and display the original ECG." This method can eliminate the motion artifacts so long as the patient's ECG signal remains static. However, if there is a change in the ECG signal during an MRI scan, the signal processor subtracting the motion artifact may interpret this as a change in the motion artifact, since a dynamic change in the patient's ECG signal and a change in the motion artifact are indistinguishable except through the manipulation of data previously collected. This can result in inaccurate ECG measurements being output.

It is therefore an objective of the present invention to provide a method and system for reducing motion artifacts in ECG measurements made in strong magnetic fields.

It is yet another objective of the present invention to provide a system for reducing motion artifacts in ECG measurements made in strong magnetic fields in which the placement of the ECG electrodes is not limited to certain positions on the patient.

It is a further objective of the present invention to provide a system for reducing motion artifacts in ECG measurements made in strong magnetic fields which operates in real time and is not dependent on prior measurements.

SUMMARY

It has now been found that these and other objects of the invention are realized by a method for eliminating a motion artifact signal in an electrocardiogram measurement of a subject in a strong magnetic field, comprising the steps of producing a predetermined signal to controllably modulate the flux density of the magnetic field while performing an electrocardiogram measurement of a subject in the magnetic field to produce a first electrocardiogram signal; using the predetermined signal to extract a motion artifact signal from the first electrocardiogram signal; and subtracting the extracted motion artifact signal from the first electrocardiogram signal, thereby creating an output electrocardiogram signal free of the motion artifact signal.

More specifically, the stated and other objects of the invention are realized by an apparatus for eliminating a motion artifact signal in an electrocardiogram measurement of a subject in a magnetic resonance imaging machine which includes primary modulation coils for creating a strong magnetic field in the magnetic imaging machine, comprising means for performing an electrocardiogram measurement of a subject in the strong magnetic field to produce a first electrocardiogram signal; a modulation waveform generator for generating a predetermined signal; a modulation coil driver coupled to the modulation waveform generator and to the primary modulation coils for supplying a current proportional to the predetermined signal to the primary modulation coils; a sample and hold timing generator coupled to the modulation waveform generator for producing a first sampling signal and a second sampling signal in timed relationship with the predetermined signal; a first sample and hold circuit coupled to the sample and hold timing generator and to the electrocardiogram measurement means for sampling the first electrocardiogram signal based upon the first sampling signal to produce a first error correction signal; a second sample and hold circuit coupled to the sample and hold timing generator and to the electrocardiogram measurement means for sampling the first electrocardiogram signal based upon the second sampling signal to produce a second error correction signal; a first subtraction circuit coupled to the first sample and hold circuit and to the second sample and hold circuit for subtracting the first error correction signal from the second error correction signal, thereby creating an extracted motion artifact signal; and a second subtraction circuit coupled to receive the motion artifact signal and the first electrocardiogram signal for subtracting the extracted motion artifact signal from the first electrocardiogram signal, thereby creating an output electrocardiogram signal free of the motion artifact signal.

In particular, the subject invention is an apparatus and method for eliminating a motion artifact signal in an electrocardiogram measurement of a subject in a strong magnetic field, in which the flux density of the magnetic field is modulated with a predetermined modulation signal. Modulation field coils are excited with a current proportional to the predetermined modulation signal to accomplish the modulation of the magnetic field. The electrocardiogram of a subject in the magnetic field is measured, producing a first signal including the motion artifact. A signal substantially equal to the motion artifact signal is extracted from the first electrocardiogram signal by generating a first sampling signal and a second sampling signal in timed relationship with the predetermined modulation signal, and then separately sampling the first electrocardiogram signal based upon the first sampling signal and upon the second sampling signal, producing a first error correction signal based upon the first sampling and a second error correction signal based upon the second sampling. The second error correction signal is subtracted from the first error correction signal, producing a third error correction signal, which is filtered and amplified to produce the extracted motion artifact signal. The extracted motion artifact signal is subtracted from the first electrocardiogram signal, which may be passed through a slew rate filter before the subtraction, creating an output electrocardiogram signal substantially free of the motion artifact signal.

In the preferred embodiment of the apparatus of the present invention, the electrocardiogram measurement is performed by means of electrodes attached to the subject in the strong magnetic field by leads that are in turn attached to the input of an electronics module with circuitry for performing the first electrocardiogram measurement and for extracting the motion artifact signal. The output signal from the electronics module consisting of the electrocardiogram signal without the motion artifact is supplied to an electrocardiogram display outside the strong magnetic field.

The preferred embodiment of the apparatus of the present invention includes primary field modulation coils for the purpose of varying the strong magnetic field. The electronics module also includes a modulation waveform generator for generating the predetermined modulation signal, a modulation coil driver coupled to the modulation waveform generator and to the primary modulation coils for supplying a current proportional to the predetermined modulation signal thereto, a sample and hold timing generator coupled to the modulation waveform generator for producing a first sampling signal and a second sampling signal in timed relationship with the predetermined modulation signal, a first sample and hold circuit coupled to the sample and hold timing generator and to the input differential amplifier for sampling the first electrocardiogram signal based upon the first sampling signal and producing a first error correction signal, a second sample and hold circuit coupled to the sample and hold timing generator and to the input differential amplifier for sampling the first electrocardiogram signal based upon the second sampling signal and producing a second error correction signal, an intermediate differential amplifier which is coupled to the outputs of the two sample and hold circuits for subtracting the first error correction signal from the second error correction signal to create a third error correction signal. The electronics module further includes a filter/amplifier coupled to the intermediate differential amplifier for filtering and amplifying the third error correction signal and creating an extracted motion artifact signal, an output differential amplifier coupled to the filter/amplifier and to the input differential amplifier for subtracting the extracted motion artifact signal from the first electrocardiogram signal and creating an output electrocardiogram signal free of the motion artifact signal. Finally, the electronics module includes means for transmitting the output cardiogram signal to an electrocardiogram monitor for displaying the output cardiogram signal.

BRIEF DESCRIPTION OF THE DRAWINGS

The above and related objects, features and advantages of the present invention will be more fully understood by reference to the following detailed description of the presently preferred, albeit illustrative, embodiments of the present invention when taken in conjunction with the accompanying drawing wherein.

DETAILED DESCRIPTION OF THE PREFERRED EMBODIMENTS

Figure 1:
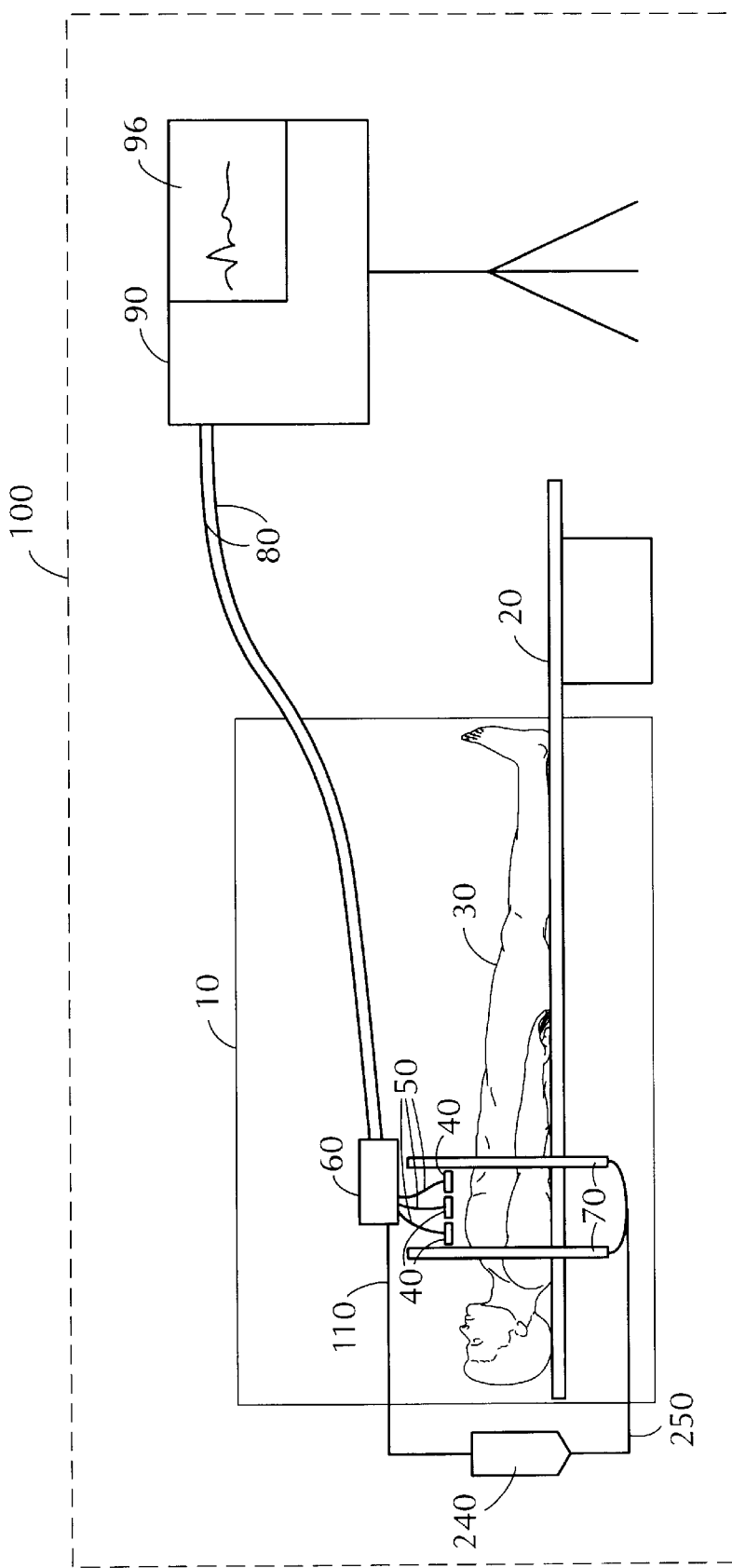
FIG. 1 is a block diagram of the invention.

Referring now to the drawings, and in particular to FIG. 1, an MRI machine 10 with patient bed 20 is shown inside a magnet room 100. Preferably, three electrodes 40 are attached to patient 30 lying on bed 20 and are connected by leads 50 to an electronics module 60 located in the tunnel which contains the ECG electronics sensor and motion artifact compensator. Preferably, two fiber optic cables 80 connect electronics module 60 to ECG monitor 90 located outside the MRI machine 10 but elsewhere within the magnet room 100. A third fiber optic cable 110 connects the electronics module 60 to the modulation coil driver 240, which is located outside of the patient tunnel inside MRI machine 10. As will be described in further detail with respect to FIG. 2 below, modulation coil driver 240 is connected to the primary field modulation coils 70 by cable 250 to provide an excitation current thereto. In this embodiment, the primary field modulation coils 70 are added to an existing MRI machine 10.

Figure 2:
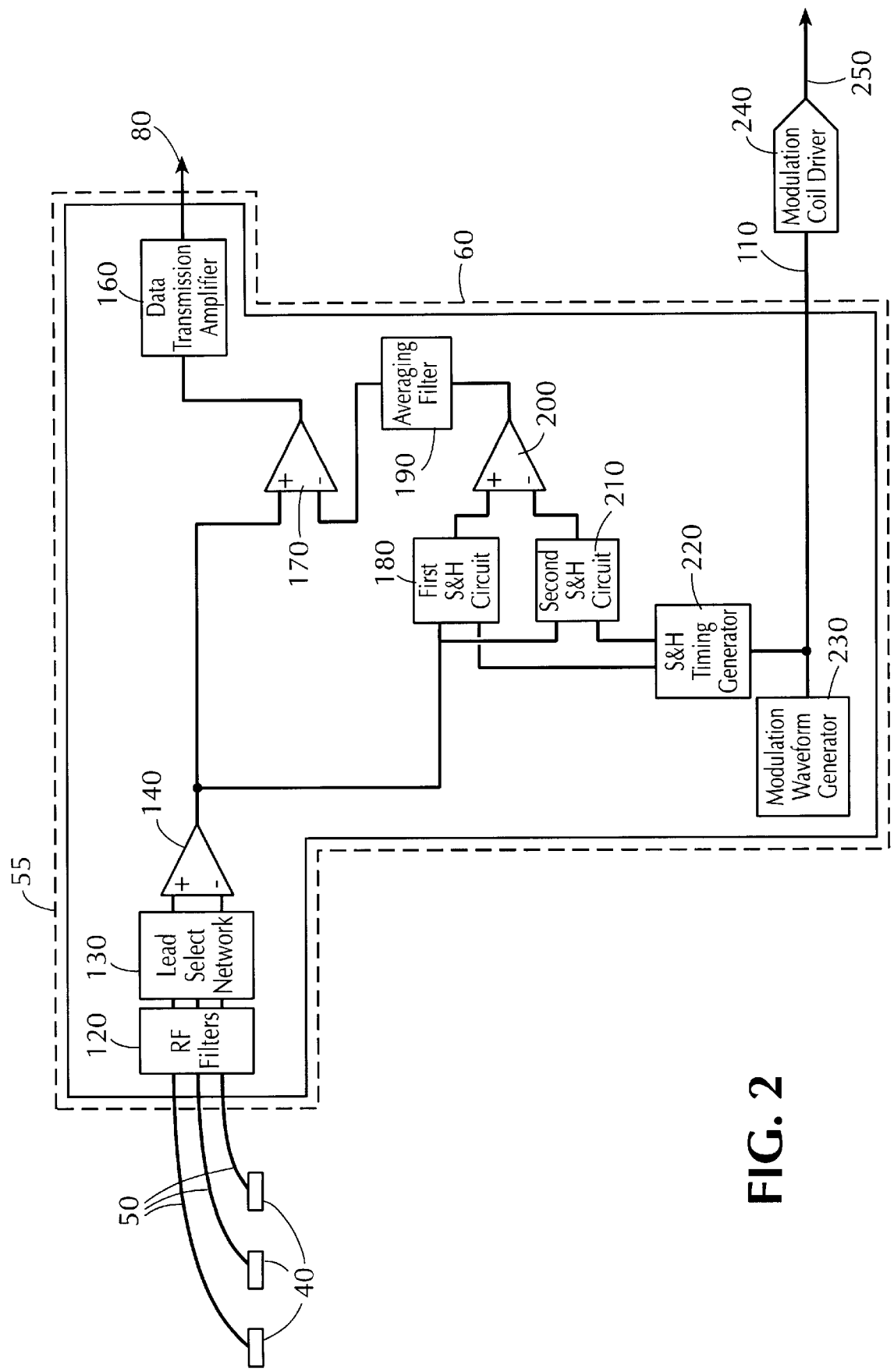
FIG. 2 is a preferred embodiment of the ECG and motion artifact compensation electronics module of the present invention.

Referring to FIG. 2, three electrodes 40 are preferably connected to the electronics module 60 through RF filter 120 by short high resistance leads 50. Preferably, the electrodes 40 and the leads 50 are positioned within the cylindrical volume defined by the two primary field coils 70. A Faraday shield 55 preferably surrounds the ECG electronics sensor module 60 with RF filter 120 at the input port of Faraday shield 55. RF filter 120 and Faraday shield 55 protect the electronics circuitry within electronics module 60 from high frequency noise generated in the MRI machine 10. The output of RF filter 120 is applied to conventional lead select network 130 which is controlled to select a pair of leads 50 as active leads. The pair of active leads are input to differential amplifier 140. ECG signals from the active leads are amplified by differential amplifier 140. In a conventional ECG amplifier, the signal output from differential amplifier 140 would then be input to the data transmission amplifier 160 for transmission to the ECG monitor 90.

However, in the present invention, the output of different amplifier 140, which represents the measured ECG signal, is applied to the positive input terminal of differential amplifier 170.

In addition, in accordance with the present invention, the output of differential amplifier 140 is also applied as the input signal to first sample & hold circuit 180 and second sample & hold circuit 210. A modulation waveform generator 230 preferably generates a pulse signal having a trapezoidal waveform, which, in the preferred embodiment, has 0.3 ms rise and fall times and a pulse width of 1.6 ms, similar in shape to a typical MRI read out gradient pulse. The period of the pulse signal is 20 ms. The modulation waveform generator 230 output is applied to sample & hold timing generator 220 and through fiber optic cable 110 to modulation coil driver 240. Modulation coil driver 240 is a voltage to current converter that is used to drive primary field modulation coils 70 which are added to MRI machine 10 as part of the present invention. The modulation field coils 70 are a Helmholtz pair in which each circular coil is at least 50 cm in diameter, large enough to encircle the shoulders and chest of the patient 30 when inside the MRI machine 10, and is made up of a number of turns of closely wound insulated wire. When operating in the strong magnetic field, the planes of the coils 70 are parallel with each other and the coils 70 are spaced half the coil diameter apart. The common axis of the coils is parallel to the axis of the tunnel inside the MRI machine 10. The coils 70 are electrically connected, such that when energized, their magnetic fields are aiding. The coils 70 may be mounted permanently inside the MRI machine 10, or mounted to the patient bed 20 so that the coils 70 move in and out of the MRI machine 10 with the patient 30. In either case, the coils 70 must surround the volume of space that includes the heart and large vessels of the patient 30 while the ECG is being measured in the strong magnetic filed of the MRI machine 10. The pulsed current in primary field modulation coils 70 causes the flux density $\beta$ in the MRI machine 10 to change momentarily by a fixed amount $\Delta\beta$ at the predetermined repetition rate of the pulse signal produced by waveform generator 230. This causes the primary field of the MRI machine 10 to alter its flux density in a uniform manner in the volume of space that includes the heart and large vessels of patient 30, and the ECG electrodes 40 and leads 50 where the motion artifact signals are generated.

It is well known that when a conducting medium moves with velocity v in a magnetic field which has a flux density $\beta$, an electric potential e is induced in the conductor such that:

$$e = -\beta * k * v \quad (1)$$

where k is a proportionality constant. The blood flow motion artifact in accordance with Equation (1) is produced because the patients blood is a conducting medium which flows in the aorta relative to the strong magnetic field. The extraneous electrical potential e produced by the flow of blood through the patient's aorta combines with the ECG potential and the combination is sensed by the ECG monitor. In other words, the signal measured by the ECG system includes a cardiac (i.e., the actual ECG) signal component c and a motion artifact component e, such that $$\text{measured ECG} = c + e \quad (2)$$

Since a part of the motion artifact e resembles the ECG signal in both amplitude and waveform, the measured ECG signal is often useless for either diagnostic or timing purposes. Moreover, the value of e cannot be calculated because k and v are unknown. However, with the addition of the modulation waveform generator 230, the modulation coil driver 240 and the primary modulation coils 70, and the creation of the predetermined pulsed current that is applied to the primary field modulation coils 70 in accordance with this invention, the flux density $\beta$, is changed in time in a controlled manner permitting the computation and elimination of the motion artifact signal e and the accurate display of the patient's actual ECG signal.

More specifically, a current pulse having a preselected magnitude and duration of 1.6 ms is produced by modulation coil driver 240 thereby creating a changing $\Delta\beta$ in the flux density of the magnetic field in the MRI machine. The changed flux density of the magnetic field in the MRI machine, now equal to $\beta + \Delta\beta$, creates a modified induced electric potential e' in the measured ECG signal according to the following formula:

$$e' = -(\beta + \Delta\beta) * k * v = -(\beta * k * v + \Delta\beta * k * v) = e + \Delta e = (1 + \Delta) * e \quad (3)$$

The magnitude of the current pulse, and therefore $\Delta\beta$, is preselected and can be controlled by the amount of current applied to the primary modulation coils 70 by the modulation coil driver 240 in conjunction with the design of the primary modulation coils 70. In the preferred embodiment of the present invention, the current pulse produced by modulation coil driver 240 is selected to create a $\Delta$ equal to 0.0025.

Figure 3A:
FIG. 3A is a graph of a normal ECG waveform when taken outside the strong magnetic field.
Figure 3B:
FIG. 3B is a graph of a normal ECG waveform when taken within the strong magnetic field.
Figure 3C:
FIG. 3C is a graph of a normal ECG waveform when taken within a strong magnetic field that is being modulated.
Figure 3D:
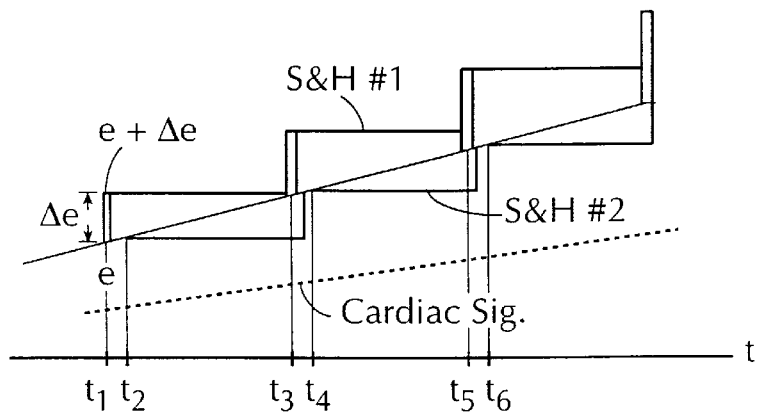
FIG. 3D is an expanded view of FIG. 3C.

Referring to FIG. 3C, the $\Delta e$ signals are shown in exaggerated magnitude riding on top of the measured ECG signal. Note that the magnitude of the $\Delta e$ pulses shown in FIG. 3C is proportional to the magnitude of the e signal, i.e., the difference between the solid line and the dotted line, as follows from Equation (3). FIG. 3D is an expanded view of the rising portion of the measured ECG waveform showing that the motion artifact has a potential of $e + \Delta e$ during the 1.6 ms duration of the pulse produced by modulation waveform generator 230, and a potential of e at all other times. In accordance with the present invention, a first error correction signal, $s_1$, is created which represents a stepwise approximation of the modified measured ECG signal including $\Delta e$ by sampling the measured ECG signal during the time in which the pulse is present. A second error correction signal, $s_2$, is created which represents a stepwise approximation of the unmodified measured ECG signal without the $\Delta e$ by sampling the ECG signal shortly after the cessation of the pulse. The second error correction signal is subtracted from the first error correction signal to extract an approximation of the $\Delta e$ signal, as shown by the following formula:

$$s_1 - s_2 = (c + e + \Delta e) - (c + e) = \Delta e \quad (4)$$

Once the approximation of the $\Delta e$ signal is extracted, since the $\Delta$ factor is known, multiplying $\Delta e$ by a factor equal to $1/\Delta$ provides an approximation of e, which is then subtracted from the measured ECG signal to provide an output ECG signal which is a much more accurate representation of the cardiac signal c.

Figure 3E:
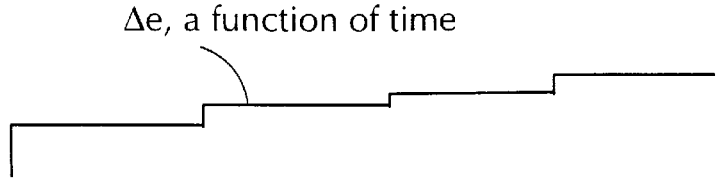
FIG. 3E is an expanded view of the stepwise representation of the extracted error signal $\Delta e$ that appears at the output of differential amplifier 200 of FIG. 2.

Referring back to FIG. 2, sample and hold timing generator 220 creates two different timing pulse signals. The first timing pulse signal is input to first sample & hold 180 to permit the sampling of the measured ECG signal during the time when the flux density of the strong magnetic field is increased to $\beta + \Delta\beta$. The measured ECG signal is the other input signal to first sample & hold 180. FIG. 3D shows how the measured ECG signal is sampled by first sample & hold 180 at times $t_1$, $t_3$ and $t_5$. The output of first sample & hold 180 will therefore be the first error correction signal $s_1$, which is the stepwise approximation of the measured ECG signal including the $e+\Delta e$ signal. The output of first sample & hold 180 is applied to the positive input of differential amplifier 200. The second timing pulse created by sample and hold timing generator 220 is input to second sample & hold 210 to permit sampling of the measured ECG signal when the flux density of the magnetic field is at its nominal value $\beta$. The second input to second control sample & hold 210 is also the measured ECG signal. FIG. 3D shows how the measured ECG signal is sampled by sample & hold 210 at times $t_2$, $t_4$ and $t_6$. The output of second sample & hold 210 is the second error correction signal $s_2$ which is the stepwise approximation of the measured ECG signal without the $\Delta e$ signal. The output of second sample & hold 210 is applied to the negative input of differential amplifier 200. Differential amplifier 200 subtracts $s_1$ from $s_2$, as shown in Equation (4). The output of differential amplifier 200 is therefore equal to a stepwise approximation of $\Delta e$, as shown in FIG. 3E. This stepwise approximation of $\Delta e$ is applied to averaging filter 190, which has a gain of $1/\Delta$ (i.e., 400 in the preferred embodiment). The output of averaging filter 190, which is a close approximation of motion artifact e over time, is applied to the negative input of differential amplifier 170. Since the positive input of differential amplifier 170 is the measured ECG signal (i.e., c+e), the output of differential amplifier 170 is an output signal representative of the actual cardiac signal.

The signal output from differential amplifier 170 is input to the data transmission amplifier 160. The ECG signal from data transmission amplifier 160 is received, demodulated and displayed visually on display 96 for the operator.

An important consideration with respect to the design of sample & hold circuits 180 and 210, differential amplifier 200 and averaging filter 190 is the signal to noise ratio, since the magnitude of the $\Delta e$ signal component of the measured ECG signal output from differential amplifier 140 (with a gain of approximately 400) will be approximately 1 mv maximum. Thus, as one reasonably skilled in the art would expect, careful selection of these components is necessary to ensure proper operation. In particular, the selection of low noise components and careful attention to the circuit board layout is required to ensure optimum results. In addition, if a monolithic sample and hold such as part no. LF398A from National Semiconductor is chosen, accompanying circuits should be used to minimize any extraneous noise signals, such as DC and AC zeroing circuits and sample input averaging circuits, as are well known to one reasonably skilled in the art.

In addition, all components in electronics module 60 must be non-magnetic and any electrical conductive material in electronics module 60, such as circuit board runs and Faraday shield 55 should be thin consistent with other performance requirements.

Although the preferred embodiment of his invention uses fiber optic cables for communication between the electronics module 60 and monitor 90, many methods which minimize motion induced signals can be utilized, including, but not limited to, fiber optics, IR, ultrasound and RF (at frequencies greater than approximately 400 MHz) to exit the MRI machine 10. In addition, many methods of encoding and decoding the information may be employed for information transmission and reception, including but not limited to, pulse width modulation, amplitude modulation of a sine wave, frequency modulation of a sine wave, frequency modulation of a pulse train, and digital communications.

The present invention has been shown and described as an addition to an existing MRI machine, in which the primary magnetic field therein is uniformly modulated by the addition of additional coils. However, it should be noted that the present invention is similarly applicable to any situation where it is necessary to perform an ECG measurement within a strong magnetic field. In addition, the present invention can also be integrated into the design of new MRI machines or other equipment which generates strong magnetic fields.

To summarize, the present invention provides a method and apparatus for reducing motion artifacts in ECG measurements made in a strong magnetic field, such as found in an MRI machine. In addition, the present invention reduces motion artifacts in ECG measurements made in a strong magnetic field without limiting the placement of the ECG electrodes to certain positions on the patient. Further, the present invention reduces motion artifacts in ECG measurements made in a strong magnetic field in real time and without any dependence on prior measurements.

Now that the preferred embodiments of the present invention have been shown and described in detail, various modifications and improvements thereon will become readily apparent to those skilled in the art. Accordingly, the spirit and scope of the present invention is to be construed broadly and limited only by the appended claims, and not by the foregoing specification.

We claim:

1. A method for eliminating a motion artifact signal in an electrocardiogram measurement of a subject in a strong magnetic field, comprising the steps of:

(A) producing a predetermined signal which controllably modulates the flux density of a magnetic field while performing an electrocardiogram measurement of a subject in said magnetic field to produce a first electrocardiogram signal;

(B) using said predetermined modulation signal to extract a motion artifact signal from said first electrocardiogram signal; and (C) subtracting said extracted motion artifact signal from said first electrocardiogram signal, thereby eliminating the motion artifact signal and creating an output electrocardiogram signal free of said motion artifact signal.

2. The method of claim 1, wherein the step of producing a predetermined signal which controllably modulates the flux density of a magnetic field includes the step of exciting modulation field coils with a current proportional to said predetermined signal.

3. The method of claim 1, wherein the step of using said predetermined modulation signal to extract a motion artifact signal comprises the steps of:

generating a first sampling signal and a second sampling signal in timed relationship with said predetermined signal;

sampling said first electrocardiogram signal based upon said first sampling signal to produce a first error correction signal;

sampling said first electrocardiogram signal based upon said second sampling signal to produce a second error correction signal; and subtracting said second error correction signal from said first error correction signal to produce said extracted motion artifact signal.

4. An apparatus for eliminating a motion artifact signal in an electrocardiogram measurement of a subject in a strong magnetic field apparatus which includes primary modulation coils for modulating said magnetic field, comprising:

(A) means for performing an electrocardiogram measurement of a subject in a magnetic field and thereby producing a first electrocardiogram signal;

(B) a modulation waveform generator for generating a predetermined modulation signal;

(C) a modulation coil driver coupled to said modulation waveform generator and to the primary field modulation coils for supplying a current proportional to said predetermined modulation signal to said primary field modulation coils;

(D) a sample and hold timing generator coupled to said modulation waveform generator for producing a first sampling signal and a second sampling signal in timed relationship with said predetermined modulation signal;

(E) a first sample and hold circuit coupled to said sample and hold timing generator and to said electrocardiogram measurement means for sampling said first electrocardiogram signal in timed relationship with said first sampling signal to produce a first error correction signal;

(F) a second sample and hold circuit coupled to said sample and hold timing generator and to said electrocardiogram measurement means for sampling said first electrocardiogram signal in timed relationship with said second sampling signal to produce a second error correction signal;

(G) a first subtraction circuit coupled to said first sample and hold circuit and to said second sample and hold circuit for subtracting said first error correction signal from said second error correction signal, thereby creating an extracted motion artifact signal; and (H) a second subtraction circuit coupled to receive said motion artifact signal and said first electrocardiogram signal for subtracting said extracted motion artifact signal from said first electrocardiogram signal, thereby creating an output electrocardiogram signal free of said motion artifact signal.

5. The apparatus of claim 4, further comprising:

(I) a electrocardiogram monitor for displaying said output cardiogram signal; and (J) a means for conveying said output cardiogram signal from said second subtraction circuit to said electrocardiogram monitor.

6. The apparatus of claim 4, wherein said means for performing an electrocardiogram measurement comprises:

at least three electrodes coupled to said subject;

a lead select network coupled to said electrodes; and a differential amplifier coupled to said lead select network for producing a first electrocardiogram signal.

7. The apparatus of claim 6, further comprising:

a data transmission amplifier coupled to said second subtraction circuit;

an electrocardiogram monitor for displaying said output cardiogram signal; and data transmission means connecting said data transmission amplifier to said electrocardiogram monitor for conveying said output cardiogram signal from said data transmission amplifier to said electrocardiogram monitor.

8. The apparatus of claim 7, wherein said lead select network, said differential amplifier, said second subtraction circuit, said data transmission amplifier, said first subtraction circuit, said first sample and hold, said second sample and hold, said sample and hold timing generator, and said modulation waveform generator are mounted within an enclosure which can be positioned next to the patient in the strong magnetic field apparatus.

9. An apparatus for eliminating a motion artifact signal in an electrocardiogram measurement of a subject in a strong magnetic field, comprising:

(A) means producing a predetermined signal to controllably modulate the flux density of a strong magnetic field;

(B) means for performing an electrocardiogram measurement of a subject in said strong magnetic field to produce a first electrocardiogram signal;

(C) means for extracting a motion artifact signal from said first electrocardiogram signal using said predetermined signal; and (D) a subtraction circuit for subtracting said motion artifact signal from said first electrocardiogram signal, thereby creating an output electrocardiogram signal free of said motion artifact signal.

* * * * *